(12) United States Patent
Lee et al.

(10) Patent No.: US 8,524,914 B2
(45) Date of Patent: Sep. 3, 2013

(54) METHOD FOR PREPARING ROSUVASTATIN, INTERMEDIATE COMPOUNDS USEFUL FOR PREPARING SAME, AND METHOD FOR PREPARING SAME

(75) Inventors: Hongwoo Lee, Hwaseong-si (KR); Daejong Park, Gunpo-si (KR); Choongleol Yoo, Incheon (KR); Donghyuk Nam, Seoul (KR); Hohyung Ryu, Cheonan-si (KR); Dongjin Kim, Cheonan-si (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 13/376,173

(22) PCT Filed: Apr. 8, 2010

(86) PCT No.: PCT/KR2010/002169
§ 371 (c)(1),
(2), (4) Date: Feb. 10, 2012

(87) PCT Pub. No.: WO2010/140765
PCT Pub. Date: Dec. 9, 2010

(65) Prior Publication Data
US 2012/0136151 A1   May 31, 2012

(30) Foreign Application Priority Data
Jun. 5, 2009 (KR) .................. 10-2009-0050044

(51) Int. Cl.
*C07D 235/04* (2006.01)
*C07D 257/04* (2006.01)
*C07D 277/62* (2006.01)

(52) U.S. Cl.
USPC .................. 548/304.7; 548/166; 548/251

(58) Field of Classification Search
USPC ................. 548/152, 166, 251, 304.7
See application file for complete search history.

(56) References Cited

U.S. PATENT DOCUMENTS

| RE37,314 E | 8/2001 | Hirai et al. | 514/316 |
| 6,833,461 B2 | 12/2004 | Hong et al. | 549/292 |
| 6,875,867 B2 * | 4/2005 | Brodfuehrer et al. | 540/577 |
| 8,178,697 B2 | 5/2012 | Ahn et al. | 548/405 |
| 2011/0015407 A1 | 1/2011 | Ahn et al. | 548/405 |

FOREIGN PATENT DOCUMENTS

| EP | 0521471 | 10/2000 |
| KR | 10-0648160 | 11/2006 |
| WO | WO 00/49014 | 8/2000 |
| WO | WO 03/087112 | 10/2003 |
| WO | WO 2004/052867 | 5/2004 |
| WO | WO 2007/007119 | 1/2007 |
| WO | WO 2007/125547 | 11/2007 |
| WO | WO 2010/140765 | 12/2010 |

OTHER PUBLICATIONS

Letter/Written Disclosure of the Supplemental Information Disclosure Statement for the above-referenced application, mailed on Mar. 6, 2012, 2 pages.
Derwent English abstract for WO 2010/140765, published Dec. 9, 2010 entitled: "New intermediate compounds used in preparing rosuvastatin or their salts, preferably hemi-calcium salts," Dialog File No. 351, Accession Nbr. 21396770, 4 pages.
International Search Report, issued Jan. 25, 2011, in conncection with International Patent Application No. PCT/KR2010/002169, 5 pages.
Written Opinion, issued Jan. 25, 2011, in conncection with International Patent Application No. PCT/KR2010/002169, 5 pages.
International Preliminary Report on Patenability, issued Dec. 6, 2011, in connection with International Patent Application No. PCT/KR2010/002169, 6 pages.
Letter/Written Disclosure of the Supplemental Information Disclosure Statement for the above-referenced application, mailed on Mar. 28, 2013, 2 pages.
Supplementary European Search Report and Written Opinion, issued Oct. 9, 2012, in connection with European Patent Application No. EP 10 78 3514, 4 pages.

\* cited by examiner

*Primary Examiner* — Golam M M Shameem
(74) *Attorney, Agent, or Firm* — McKenna Long & Aldridge LLP; Stephanie Seidman

(57) ABSTRACT

The present invention relates to novel intermediate compounds used in preparing Rosuvastatin or the pharmaceutically acceptable salts thereof, to a method for preparing same, and to a method for preparing Rosuvastatin or the pharmaceutically acceptable salts thereof from the intermediates. The preparation method of the present invention has the effect of providing Rosuvastatin hemi-calcium salts with an excellent yield rate.

5 Claims, No Drawings

METHOD FOR PREPARING ROSUVASTATIN, INTERMEDIATE COMPOUNDS USEFUL FOR PREPARING SAME, AND METHOD FOR PREPARING SAME

RELATED APPLICATIONS

This application is the National Stage of International Application. No. PCT/KR2010/002169, filed 8 Apr. 2010, which claims benefit of priority to KR 10-2009-0050044, filed 5 Jun. 2009, the specification of which is incorporated by reference herein.

TECHNICAL FIELD

The present invention relates to novel intermediate compounds used in the preparation of rosuvastatin or a pharmaceutically acceptable salt thereof, a method for preparing the same, and a method for preparing pharmaceutically acceptable rosuvastatin from the same intermediates.

BACKGROUND ART

Drugs, which show cholesterol-lowering effects through the mechanism of inhibiting the activity of 3-hydroxy-3-methyl-glutaryl coenzyme A reductase (HMG-CoA reductase), are generally called "statin". Among them, examples of the earliest first-generation compounds developed include simvastatin, lovastatin, and pravastatin which are fermentation products, and examples of second-generation compounds include atorvastatin, fluvastatin, rosuvastatin, and pitavastatin which are synthetic drugs.

Among these, rosuvastatin calcium has a structural formula given below and is marketed under the trademark CRESTOR™.

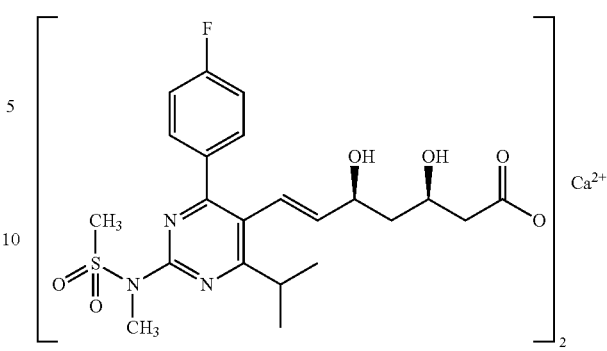

European Patent Application Publication No. EP 0521471 discloses (E)-7-[4-(4-fluorophenyl)-6-isopropyl-2-[methyl (methylsulfonyl)amino]pyrimidin-5-yl](3R,5S)-3,5-dihydroxyhept-6-enoic acid (rosuvastatin) and its sodium salt and hemicalcium salt, and a process for their preparation. According to this patent document, rosuvastatin and its pharmaceutically acceptable salts are obtained by condensation of methyl (3R)-3-[(tert-butyldimethylsilyl)oxy]-5-oxo-6-triphenylphosphoranylidene hexanoate with 4-(4-fluorophenyl)-6-isopropyl-2-(N-methyl-N-methanesulfonyl amino)-5-pyrimidinecarboxaldehyde, followed by deprotection of the 3-hydroxy group, asymmetric reduction of the 5-oxo group and hydrolysis.

Further, WO 00/49014 also discloses a process for the preparation of rosuvastatin and its pharmaceutically acceptable salts, as shown in Reaction Scheme 1 given below. The compound and its pharmaceutically acceptable salts are obtained in WO 00/49104 by reaction of N-(5-(((diphenylphosphoryl)methyl)-4-(4-fluorophenyl)-6-isopropylpyrimidin-2-yl)-N-methylmethanesulfonamide (hereinafter, referred to as "DPPO") with tert-butyl 2-[(4R,6S)-6-formyl-2,2-dimethyl-1,3-dioxan-4-yl]acetate (hereinafter, referred to as "BFA") in the presence of a base, thus preparing BEM, followed by removal of protecting groups.

[Reaction Scheme 1]

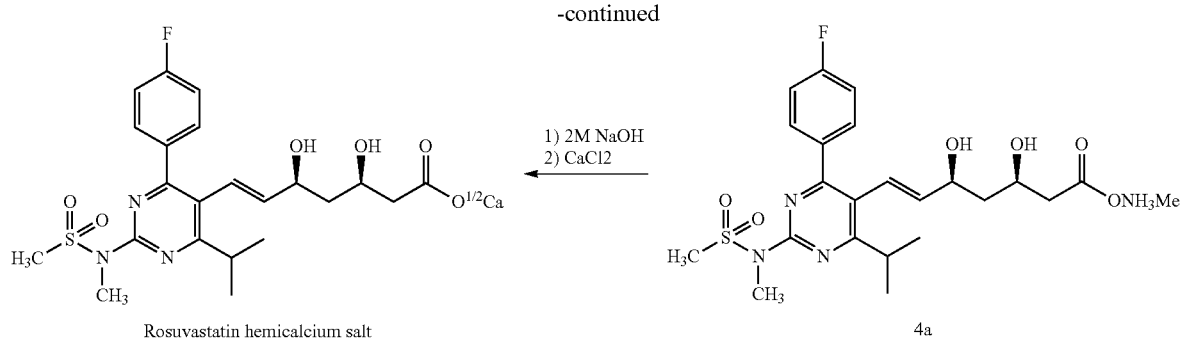

Further, WO 04/52867 discloses a process for the preparation of rosuvastatin and its pharmaceutically acceptable salts, which includes the condensation of 1-cyano-(2S)-2-[(tert-butyldimethylsilyl)oxy]-4-oxo-5-triphenylphosphoranylidene pentane with 4-(4-fluorophenyl)-6-isopropyl-2-(N-methyl-N-methanesulfonyl amino)-5-pyrimidinecarboxaldehyde, followed by deprotection, asymmetric reduction of the 4-oxo group and hydrolysis.

WO 07/007119 discloses a process for the preparation of rosuvastatin based on an asymmetric aldol reaction using a chiral titanium catalyst.

Further, WO 07/125547, as shown in Reaction Scheme 2 given below, discloses a method for preparing rosuvastatin or a pharmaceutically acceptable salt thereof, which includes reacting N-(4-(4-fluorophenyl)-6-isopropyl-5-((1-methyl-1H-benzo[d]imidazol-2-ylsulfonyl)methyl)pyrimidin-2-yl)-N-methylmethanesulfonamide (12) with t-butyl 2-((4R,6S)-6-formyl-2,2-dimethyl-1,3-dioxan-4-yl)acetate (BFA) to prepare BEM, and then removing the protecting groups.

[Reaction Scheme 2]

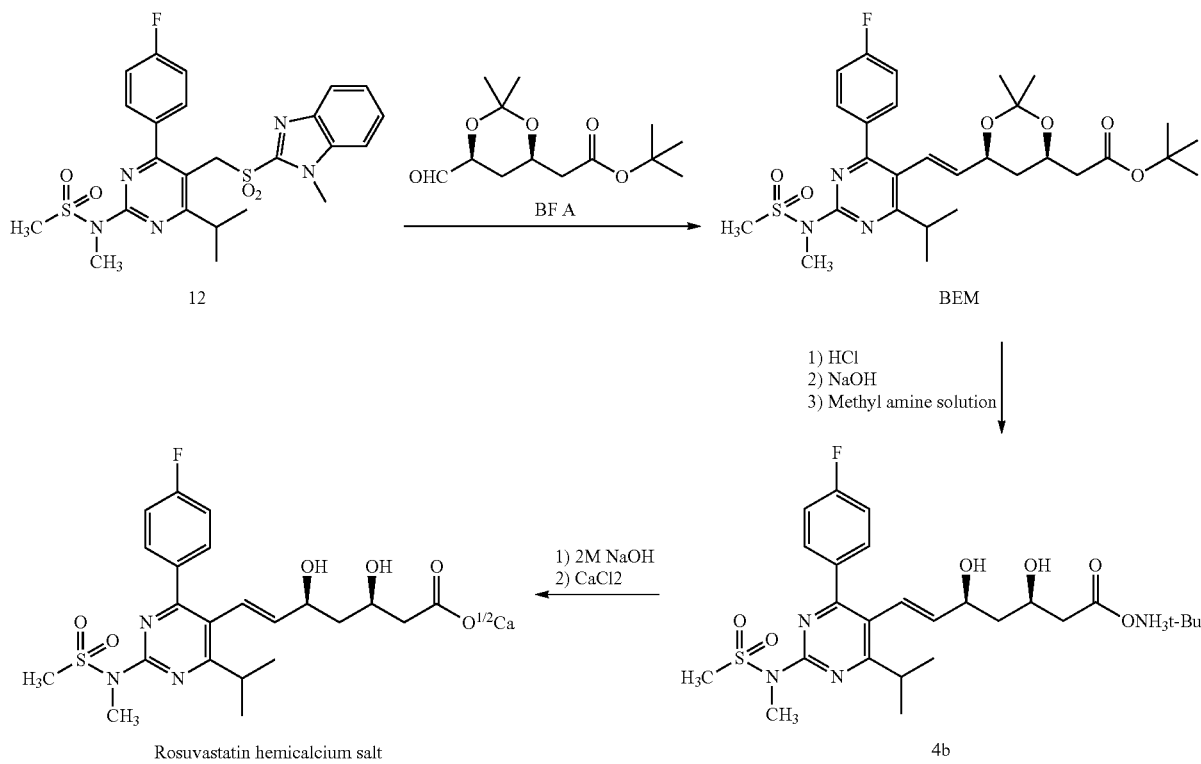

However, since currently known methods for the preparation of rosuvastatin hemicalcium salts exhibit low yield and low purity, there is a continuing need for development of alternative processes for the manufacture of pharmaceutically acceptable salts of rosuvastatin.

DISCLOSURE OF THE INVENTION

Technical Problem

Therefore, the present invention is intended to provide a method for preparing rosuvastatin or a pharmaceutically acceptable salt thereof, which is more environmentally friendly, is simpler in terms of the process, is efficient from an economic point of view, and is high in terms of yield and purity, as compared to known methods, a novel chiral intermediate compound which is applied to the same method, and a method for preparing the same novel chiral intermediate compound.

Technical Solution

The present invention provides a method for preparing a compound of formula 3, including reacting a compound of formula 1 with a compound of formula 2 in the presence of a base to prepare the compound of formula 3.

[Formula 1]

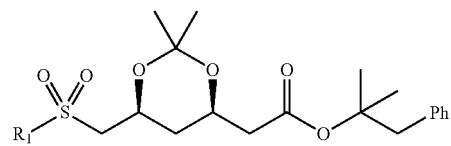

[Formula 2]

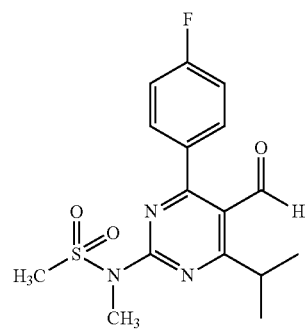

[Formula 3]

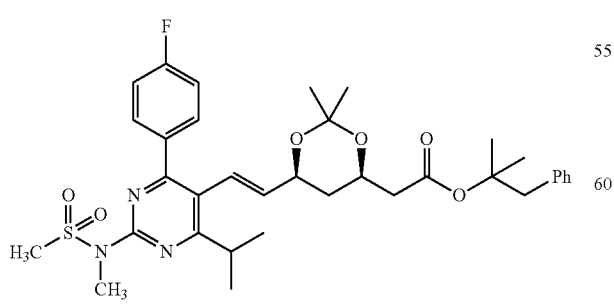

In formula 1, $R_1$ represents

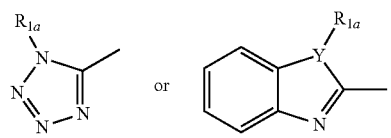

wherein Y represents a nitrogen or sulfur atom and $R_{1a}$ represents hydrogen, $C_1$-$C_4$ alkyl or phenyl.

The compound of formula 2 in accordance with the present invention is commercially available or may be prepared by a known method (for example, see U.S. RE37314). The amount of the compound of formula 2 used may be present in an excess relative to the compound of formula 1, but is preferably in a range of 1.0 to 1.35 equivalents relative to 1 equivalent of the compound of formula 1, and more preferably 1.05 to 1.15 equivalents.

In the method for preparing a compound of formula 3 in accordance with the present invention, the reaction temperature is preferably in a range of −90 to 0° C., and more preferably −80 to −40° C. Even more preferably, the reaction temperature is maintained at a temperature of −90 to −30° C. for about 2 to 4 hours and then gradually elevated to 0° C.

In the method for preparing a compound of formula 3 in accordance with the present invention, the base means a base which is capable of removing hydrogen of carbon between the sulfonyl group and the protected hydroxy group in the compound of formula 1, and examples thereof include an amide base such as lithium bis(trimethylsilyl)amide, sodium bis(trimethylsilyl)amide or potassium bis(trimethylsilyl)amide; n-butyl lithium, sodium hydride, an alkyl metal, and a metal hydride. Among these, lithium bis(trimethylsilyl)amide, sodium bis(trimethylsilyl)amide (NaHMDS) or potassium bis(trimethylsilyl)amide is preferable, and NaHMDS is more preferable.

In the method for preparing a compound of formula 3 in accordance with the present invention, the reaction is preferably carried out under the anhydrous conditions, preferably under a nitrogen or argon atmosphere. The reaction solvent is preferably an ether solvent, an aromatic solvent, or a mixture thereof, and more preferably tetrahydrofuran (THF) or a mixture of THF and toluene.

Further, the present invention provides a compound of formula 1:

[Formula 1]

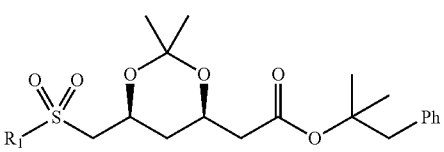

wherein $R_1$ represents

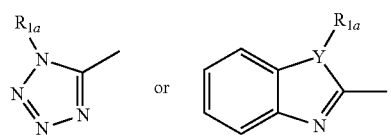

wherein Y represents a nitrogen or sulfur atom and $R_{1a}$ represents hydrogen, $C_1$-$C_4$ alkyl or phenyl.

Further, the present invention provides 2-methyl-1-phenylpropan-2-yl 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate of formula 3.

[Formula 3]

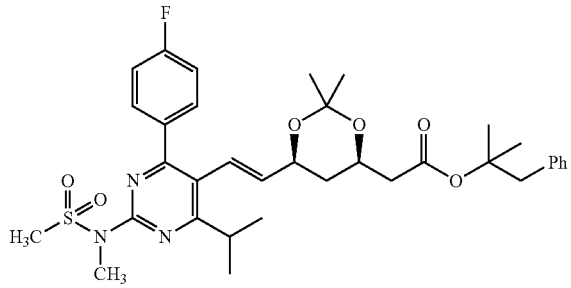

Further, the present invention provides a method for preparing a compound of formula 4, including steps of (1) removing the dihydroxy protecting group of 2-methyl-1-phenylpropan-2-yl 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate in the presence of an acid; (2) degrading the α,α-dimethylphenylethyl ester group of the product of Step (1) in the presence of a base, followed by neutralization in the presence of an acid to prepare (E)-7-[4-(4-fluorophenyl)-6-isopropyl-2-[methyl(methylsulfonyl)amino]pyrimidin-5-yl](3R,5S)-3,5-dihydroxyhept-6-enoic acid; and (3) converting the product of Step (2) into a compound of formula 4 by reaction successively with an alkylamine and a reactant that provides a pharmaceutically acceptable salt.

[Formula 4]

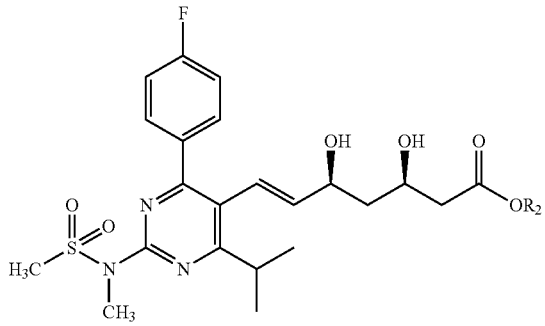

wherein $R_2$ represents a pharmaceutically acceptable cation.

As used herein, the term "pharmaceutically acceptable cation" refers to an alkali metal or alkaline-earth metal ion and an ammonium ion. Specific examples of the pharmaceutically acceptable cation include sodium, potassium, calcium, and magnesium. Calcium is particularly preferable.

In the method for preparing a compound of formula 4 in accordance with the present invention, 2-methyl-1-phenylpropan-2-yl 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate is preferably prepared by the method for preparing a compound of formula 3 in accordance with the present invention.

In Step (1) of the method for preparing a compound of formula 4 in accordance with the present invention, the acid refers to an acid used for the removal of a common hydroxy protecting group and examples thereof include hydrochloric acid, sulfuric acid, methanesulfonic acid, trifluoromethanesulfonic acid, and trifluoroacetic acid. Hydrochloric acid is preferable. The amount of the acid used may vary depending on the monovalent, divalent or trivalent acid. For example, when the acid is hydrochloric acid which is a monovalent acid, the amount of the acid used is preferably in a range of 0.02 to 0.05 equivalents, relative to 1 equivalent of 2-methyl-1-phenylpropan-2-yl 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate which is a starting material.

In Step (2) of the method for preparing a compound of formula 4 in accordance with the present invention, the base refers to a base used for the degradation of a common ester group into an alcohol and an acid, and examples thereof include sodium hydroxide, potassium hydroxide, and calcium hydroxide. Preferred is sodium hydroxide. The amount of the base used may vary depending on the monovalent, divalent or trivalent base. For example, when the base is sodium hydroxide which is a monovalent base, the amount of the base used is preferably in a range of 2 to 5 equivalents, relative to 1 equivalent of the product of Step (1).

In Step (2) of the method for preparing a compound of formula 4 in accordance with the present invention, the acid is preferably hydrochloric acid, sulfuric acid, trifluoroacetic acid, phosphoric acid, or the like.

In Step (3) of the method for preparing a compound of formula 4 in accordance with the present invention, examples of the alkylamine include methylamine, ethylamine, n-butylamine, and tert-butylamine. Preferred is methylamine.

In Step (3) of the method for preparing a compound of formula 4 in accordance with the present invention, the reactant that provides a pharmaceutically acceptable salt refers to sodium chloride, potassium chloride, magnesium chloride, calcium chloride, or the like. Calcium chloride is preferable. Step (3) of the method for preparing a compound of formula 4 in accordance with the present invention is not limited to the above-exemplified reactants and may also be carried out by a known method, for example, the method described in WO 00/49014, KR 10-0648160, WO 2007/125574, or the like.

In the method for preparing a compound of formula 4 in accordance with the present invention, the step of adding an acid to prepare rosuvastatin in Step (2) and the step of preparing the compound of formula 4 (rosuvastatin cation salt) through Step (3) are intended to improve the purity of the compound of formula 4 and therefore these steps may be omitted.

In the method for preparing a compound of formula 4 in accordance with the present invention, the reaction solvent is preferably an ether solvent such as tetrahydrofuran; an organic solvent such as acetonitrile, methanol, ethanol or isopropanol; or a mixed solvent thereof with water.

In the method for preparing a compound of formula 4 in accordance with the present invention, the reaction temperature may be appropriately selected by those skilled in the art, taking into consideration the reaction rate and the progress of side reactions. For example, the reaction temperature is preferably in a range of 0 to 50° C., and more preferably room temperature.

The method for preparing a rosuvastatin hemicalcium salt in accordance with the present invention is as shown in Reaction Scheme 3.

[Reaction Scheme 3]

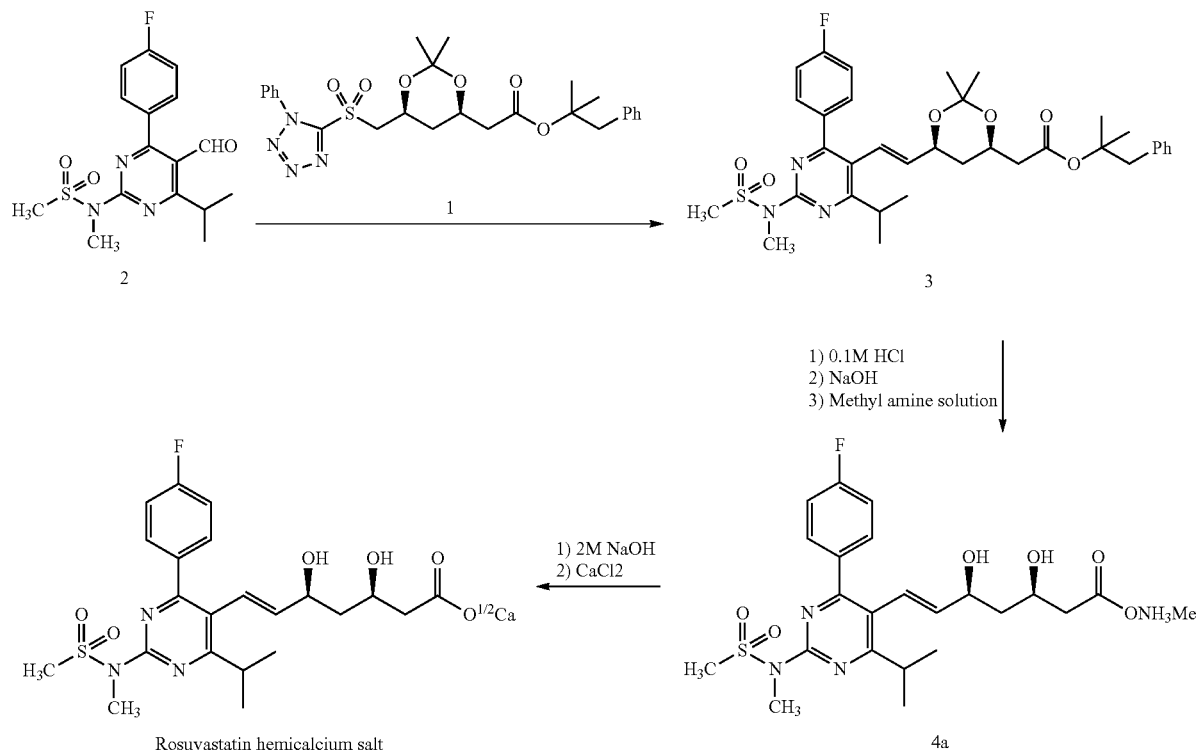

Further, the present invention provides a method for preparing a compound of formula 1 used as a starting material of the present invention in the preparation of a rosuvastatin hemicalcium salt, which includes the following steps of:

(1) reacting a compound of formula 5 with 2-methyl-1-phenylpropan-2-ylacetate in the presence of a strong base to prepare a compound of formula 7;

(2) treating the compound of formula 7 prepared in Step (1) with a reducing agent which performs stereoselective reduction through syn addition with the hydroxy group of the compound of formula 7, thereby preparing a compound of formula 8;

(3) reacting the compound of formula 8 with 2,2-dimethoxypropane in the presence of an acid catalyst to prepare a compound of formula 9;

(4) reacting the compound of formula 9 with a compound of formula 10 to prepare a compound of formula 11; and (5) treating the compound of formula 11 with an oxidizing agent to prepare the compound of formula 1.

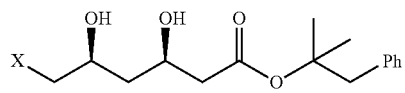

[Formula 5]

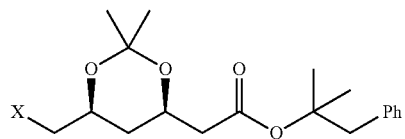

[Formula 7]

-continued

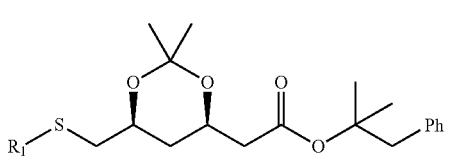

[Formula 8]

[Formula 9]

$R_1$—S—M    [Formula 10]

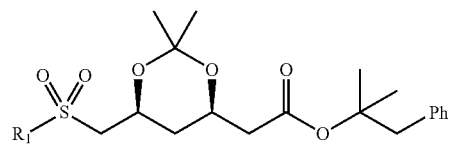

[Formula 11]

[Formula 1]

wherein X represents a halogen (iodo, bromo or chloro); $R_3$ represents $C_1$-$C_4$ alkyl; M represents a metal selected from an alkali metal or an alkaline-earth metal; and $R_1$ represents

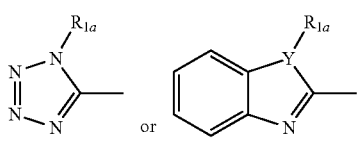

wherein Y represents a nitrogen or sulfur atom and $R_{1a}$ represents hydrogen, $(C_1-C_4)$alkyl or phenyl.

In the method for preparing a compound of formula 1 in accordance with the present invention, 2-methyl-1-phenylpropan-2-ylacetate and the compound of formula 5 are commercially available or may be prepared by a known method.

In Step (1) of the method for preparing a compound of formula 1 in accordance with the present invention, the molar ratio of the compound of formula 5:2-methyl-1-phenylpropan-2-ylacetate is most preferably in a range of 1:4 to 1:3.5. The strong base of Step (1) is selected from lithium bis(trimethylsilyl)amide, sodium bis(trimethylsilyl)amide, potassium bis(trimethylsilyl)amide, lithium diisopropylamide, and n-butyl lithium. Among these, lithium bis(trimethylsilyl)amide, sodium bis(trimethylsilyl)amide or potassium bis(trimethylsilyl)amide is preferable, and lithium bis(trimethylsilyl)amide is more preferable. Here, the amount of the base used relative to 1 equivalent of the compound of formula 5 is in a range of 1.0 to 1.2 equivalents, for example, preferably 1.05 to 1.12 equivalents. The reaction temperature is preferably in a range of –90 to 0° C., and more preferably –80 to –40° C. Even more preferably, the reaction temperature is maintained at a temperature of –90 to –30° C. for about 2 to 4 hours and then gradually elevated to 0° C. The reaction solvent may be a single solvent or a mixture of two or more solvents. For example, the reaction is carried out in an etheric solvent, an aromatic solvent, or a mixture thereof. Particularly preferred examples of the solvent include THF and a mixture of THF and toluene.

In the method for preparing a compound of formula 1 in accordance with the present invention, the reducing agent used in combination with methoxyethylborane in Step (2) is a metal borohydride which is selected from, for example, sodium borohydride, potassium borohydride or lithium borohydride. A mixture of methoxyethylborane and sodium borohydride is preferable. The reducing agent is preferably used in a molar ratio of Step (1):sodium borohydride:methoxyethylborane=1:2:2. The reaction solvent may be a single solvent selected from ethyl ether, di-n-butyl ether and tetrahydrofuran, or a mixture thereof with a solvent selected from methanol or ethanol. Among these, a mixed solvent of tetrahydrofuran and methanol is preferable. The reaction temperature is preferably in a range of –90 to 0° C., and more preferably –80 to –40° C. Even more preferably, the reaction temperature is maintained at a temperature of –90 to –30° C. for about 2 to 4 hours and then gradually elevated to 0° C.

In the method for preparing a compound of formula 1 in accordance with the present invention, the acid catalyst of Step (3) may be selected from, for example, methanesulfonic acid, p-toluenesulfonic acid, and a pyridine salt of p-toluenesulfonic acid. Preferred is methanesulfonic acid. The amount of the acid catalyst used is preferably in a range of 0.02 to 0.05 equivalents, relative to 1 equivalent of the product of Step (2). The amount of 2,2-dimethoxypropane of Step (3) used is preferably in a range of 3 to 5 equivalents, relative to 1 equivalent of the product of Step (2). The reaction solvent may be, for example, acetone, 1,4-dioxane, dichloromethane, tetrahydrofuran, or the like. Acetone is preferable. The reaction temperature is preferably room temperature of 20 to 30° C.

In the method for preparing a compound of formula 1 in accordance with the present invention, the compound of formula 10 referred to in Step (4) may be prepared by a known method, such as by reacting a commercially available thiol compound of formula "R1-SH" with sodium methoxide in an organic solvent at 0° C. For example, sodium 1-phenyl-1H-tetrazole-5-thiolate is prepared by reacting 1-phenyl-1H-tetrazole-5-thiol and sodium methoxide in a molar ratio of 1:1.1 in methanol at 0° C.

In the method for preparing a compound of formula 1 in accordance with the present invention, the reaction temperature of Step (4) is preferably in a range of 0 to 120° C., and more preferably 80 to 120° C. The reaction solvent is preferably dimethylformamide (DMF), N-methylpyrrolidinone (NMP), dimethylacetamide (DMA), toluene, or a mixture thereof.

In the method for preparing a compound of formula 1 in accordance with the present invention, the oxidizing agent used in Step (5) may be a mixture of 30% hydrogen peroxide and ammonium heptamolybdate tetrahydrate, or a mixture of meta-chloroperbenzoic acid and ammonium heptamolybdate tetrahydrate, and is preferably a mixture of 30% hydrogen peroxide and ammonium heptamolybdate tetrahydrate. The reaction solvent used may be dimethylformamide, dichloromethane, methanol, ethanol, or isopropanol. Among these, dichloromethane is preferable. The reaction temperature is in a range of –40° C. to 50° C., and preferably –10° C. to 25° C.

Further, the present invention provides a compound of formula 7, a compound of formula 8, a compound of formula 9, and a compound of formula 11, which are novel intermediates used in the preparation of the compound of formula 1:

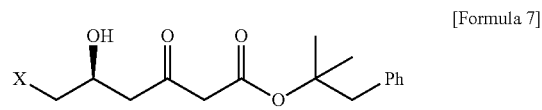

[Formula 7]

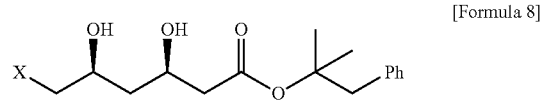

[Formula 8]

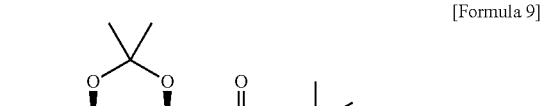

[Formula 9]

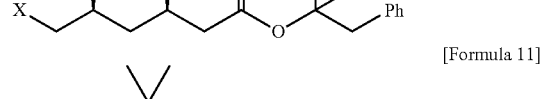

[Formula 11]

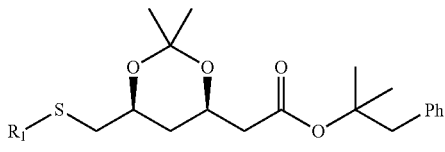

wherein X represents a halogen (chloro, bromo or iodo), and $R_1$ represents

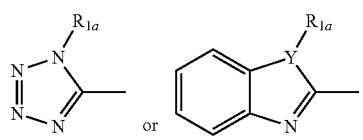

wherein Y represents a nitrogen or sulfur atom and $R_{1a}$ represents hydrogen, $(C_1-C_4)$alkyl or phenyl.

The method for preparing a compound of formula 1 in accordance with the present invention is as shown in Reaction Scheme 4.

[Reaction Scheme 4]

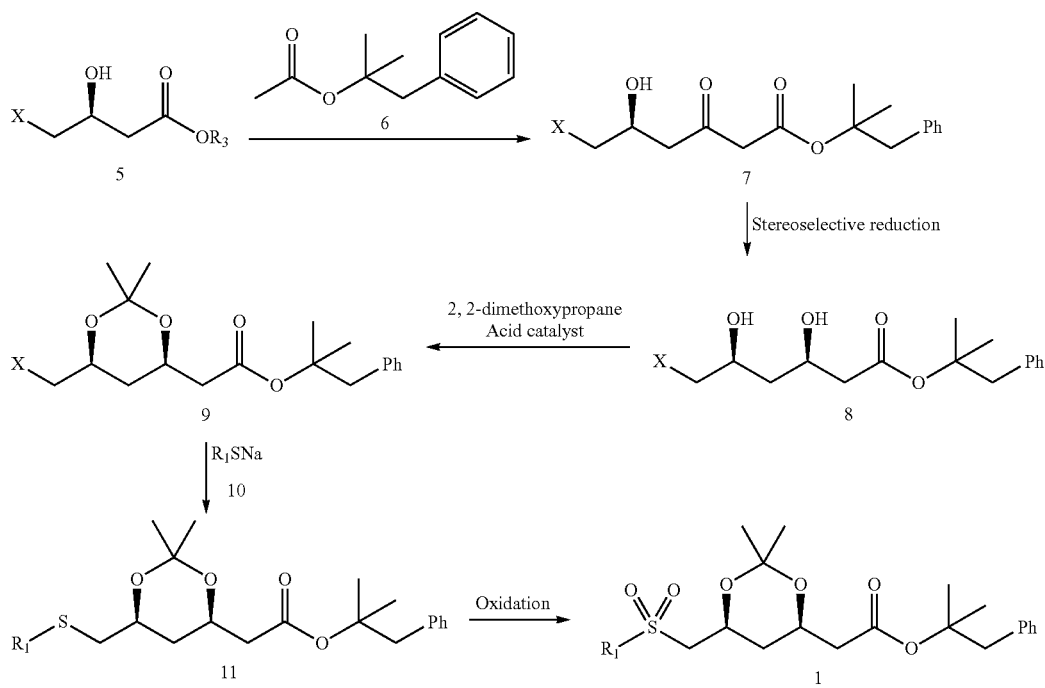

Advantageous Effects

The method for preparing rosuvastatin using novel intermediates of the present invention is simple in terms of the process, is efficient from an economic point of view, and is high in terms of yield and purity.

MODE FOR INVENTION

Hereinafter, the present invention will be described in more detail with reference to the following examples, but the present invention is not limited thereto.

Unless otherwise specifically indicated, reagents and solvents used hereinafter were purchased from Aldrich.

$^1$H-NMR data given hereinafter were measured using a Bruker DPX 400.

Example 1

Preparation of 2-methyl-1-phenylpropan-2-yl 6-chloro-5-hydroxy-3-oxohexanoate (7a)

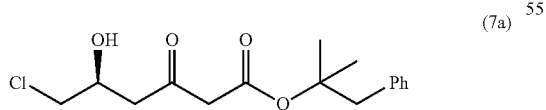

(7a)

Lithium bis(trimethylsilyl)amide (190.8 g) was dissolved in tetrahydrofuran (1400 ml) in a main reaction vessel, followed by cooling to −75° C. and nitrogen purging. 2-methyl-1-phenylpropan-2-ylacetate (219.2 g) was charged in a separate reaction vessel and was dissolved by the addition of tetrahydrofuran (300 ml), and the solution was gradually added dropwise to the main reaction vessel over 40 minutes, followed by stirring for 1 hour. (S)-ethyl 4-chloro-3-hydroxybutanoate (50 g) was added and dissolved in tetrahydrofuran (50 ml) and the resulting solution was gradually added dropwise to the main reaction vessel over 20 minutes, followed by stirring for 5 hours. Thereafter, acetic acid (124 ml) was gradually added dropwise thereto, and the temperature was gradually elevated to 0° C. Ethyl acetate (1500 ml) and purified water (1500 ml) were added thereto, followed by stirring for 10 minutes, and the organic layer was separated. The separated organic layer was washed successively with a saturated sodium chloride aqueous solution (1500 ml×2), a saturated sodium bicarbonate aqueous solution (1500 ml) and purified water (1500 ml), dried over anhydrous magnesium sulfate, and then concentrated under reduced pressure to give the crude title compound (299.0 g). A portion of the crude compound was purified by silica gel column (ethyl acetate: n-hexane=3:7(v/v)) to obtain the following NMR data.

$^1$H-NMR (400 MHz, CDCl$_3$) δ 7.34-7.18 (m, 5H), 4.35-4.30 (m, 1H), 3.65-3.60 (m, 2H), 3.42 (s, 2H), 3.01 (m, 1H), 2.80-2.75 (m, 2H), 1.99 (s, 2H), 1.50-1.46 (m, 6H)

Example 2

Preparation of 2-methyl-1-phenylpropan-2-yl 6-bromo-5-hydroxy-3-oxohexanoate (7b)

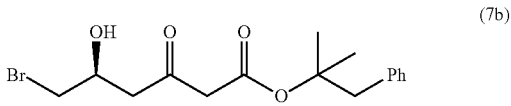 [SMILES: CC(C)(Cc1ccccc1)OC(=O)CC(=O)C[C@H](O)CCl]

(7b)

The procedure was carried out in the same manner as in Example 1, except that (S)-ethyl 4-bromo-3-hydroxybutanoate (50 g) was used in place of (S)-ethyl 4-chloro-3-hydroxybutanoate (50 g). The crude title compound was obtained (290.0 g). A portion of the crude compound was purified by silica gel column (ethyl acetate:n-hexane=3:7(v/v)) to obtain the following NMR data.

$^1$H-NMR (400 MHz, CDCl$_3$) δ 7.35-7.20 (m, 5H), 4.40-4.36 (m, 1H), 3.69-3.65 (m, 2H), 3.43 (s, 2H), 3.02 (m, 1H), 2.81-2.77 (m, 2H), 2.00 (s, 2H), 1.50-1.46 (m, 6H)

Example 3

Preparation of (3R,5S)-2-methyl-1-phenylpropan-2-yl 6-chloro-3,5-dihydroxy-hexanoate (8a)

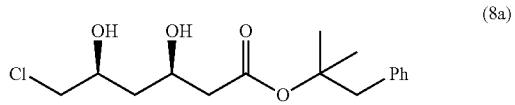 [SMILES: CC(C)(Cc1ccccc1)OC(=O)C[C@H](O)C[C@H](O)CCl]

(8a)

The crude compound 2-methyl-1-phenylpropan-2-yl 6-chloro-5-hydroxy-3-oxohexanoate (7a, 298 g) prepared in Example 1 was dissolved in a mixed solvent of tetrahydrofuran (2000 ml) and methanol (1000 ml), and the solution was cooled to −75° C. At the same temperature, methoxydiethylborane (78.8 ml) was gradually added dropwise to this solution over 20 minutes, followed by stirring for 40 minutes. Thereafter, sodium borohydride (25.0 g) was added in 5 divided portions, followed by stirring for 5 hours, and acetic acid (96 ml) was gradually added dropwise thereto. The mixture was warmed to room temperature and allowed to stand. Ethyl acetate (1800 ml) and a 3% hydrogen peroxide aqueous solution (1500 ml) were charged to the reaction section, followed by stirring for 30 minutes and extraction. The aqueous layer was reversely extracted with ethyl acetate (1000 ml), and the organic layer was combined and washed three times with a saturated sodium bicarbonate aqueous solution (1500 ml). The residue was dried over anhydrous magnesium sulfate and then concentrated under reduced pressure to give the crude title compound (13.6 g). A portion of the crude compound was purified by silica gel column (ethyl acetate:n-hexane=3:7(v/v)) to obtain the following NMR data.

$^1$H-NMR (400 MHz, CDCl$_3$) δ 7.34-7.18 (m, 5H), 4.27-4.23 (m, 1H), 4.17-4.07 (m, 1H), 3.75 (s, 1H), 3.63-3.51 (m, 2H), 3.07 (t, 2H), 2.45 (d, 2H), 1.78-1.63 (m 2H), 1.50-1.46 (m, 6H)

Example 4

Preparation of (3R,5S)-2-methyl-1-phenylpropan-2-yl 6-bromo-3,5-dihydroxy-hexanoate (8b)

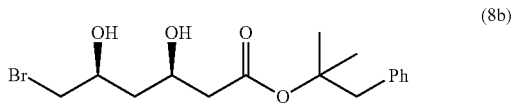

(8b)

The procedure was carried out in the same manner as in Example 3, except that the crude compound (2-methyl-1-phenylpropan-2-yl 6-bromo-5-hydroxy-3-oxohexanoate (7b, 80.0 g) prepared in Example 2 was used in place of (2-methyl-1-phenylpropan-2-yl 6-chloro-5-hydroxy-3-oxohexanoate (7a, 80.0 g). The crude title compound was obtained (12.0 g).

A portion of the crude compound was purified by silica gel column (ethyl acetate:n-hexane=3:7(v/v)) to obtain the following NMR data.

$^1$H-NMR (400 MHz, CDCl$_3$) δ 7.34-7.18 (m, 5H), 4.27-4.23 (m, 1H), 4.17-4.07 (m, 1H), 3.75 (s, 1H), 3.63-3.51 (m, 2H), 3.07 (t, 2H), 2.45 (d, 2H), 1.78-1.63 (m, 2H), 1.50-1.46 (m, 6H)

Example 5

Preparation of 2-methyl-1-phenylpropan-2-yl 2-((4R,6S)-6-(chloromethyl)-2,2-dimethyl-1,3-dioxan-4-yl)acetate

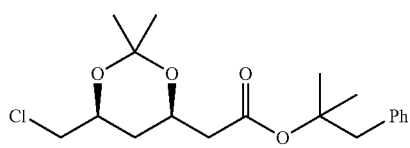 [SMILES: CC(C)(Cc1ccccc1)OC(=O)C[C@H]1C[C@@H](CCl)OC(C)(C)O1]

The crude compound (3R,5S)-2-methyl-1-phenylpropan-2-yl 6-chloro-3,5-dihydroxy-hexanoate (21.1 g) prepared in Example 3 was dissolved in acetone (210 ml), and 2,2-dimethoxypropane (65.6 ml) and methanesulfonic acid (0.2 ml) were added dropwise thereto, followed by stirring at room temperature for 2 hours. The reaction liquid was diluted with ethyl acetate (320 ml) and washed successively with a saturated sodium bicarbonate aqueous solution (320 ml), a saturated sodium chloride aqueous solution (320 ml) and purified water (320 ml). The separated organic layer was dried over anhydrous magnesium sulfate and then concentrated under reduced pressure to give the crude title compound (23.7 g).

$^1$H-NMR (400 MHz, CDCl$_3$) δ 7.30-7.18 (m, 5H), 4.30-4.27 (m, 1H), 4.14-4.10 (m, 1H), 3.54-3.40 (m, 2H), 3.15-3.06 (m, 2H), 2.52-2.34 (dd, 2H), 1.74-1.50 (m, 2H), 1.48-1.20 (m, 12H)

Example 6

Preparation of 2-methyl-1-phenylpropan-2-yl 2-((4R,6S)-6-(bromomethyl)-2,2-dimethyl-1,3-dioxan-4-yl)acetate

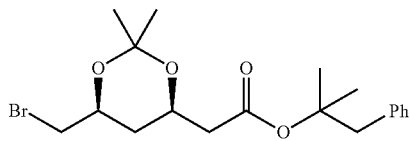 [SMILES: CC(C)(Cc1ccccc1)OC(=O)C[C@H]1C[C@@H](CBr)OC(C)(C)O1]

The procedure was carried out in the same manner as in Example 5, except that the crude compound (3R,5S)-2-methyl-1-phenylpropan-2-yl 6-bromo-3,5-dihydroxy-hexanoate (21.0 g) prepared in Example 4 was used in place of the crude compound (3R,5S)-2-methyl-1-phenylpropan-2-yl 6-chloro-3,5-dihydroxy-hexanoate (21.1 g) prepared in Example 3. The crude title compound was obtained (22.5 g).

$^1$H-NMR (400 MHz, CDCl$_3$) δ 7.31-7.20 (m, 5H), 4.32-4.29 (m, 1H), 4.17-4.13 (m, 1H), 3.57-3.44 (m, 2H), 3.18-3.09 (m, 2H), 2.53-2.37 (dd, 2H), 1.74-1.52 (m, 2H), 1.48-1.22 (m, 12H)

Example 7

Preparation of Sodium 1-phenyl-1H-tetrazole-5-thiolate (10a)

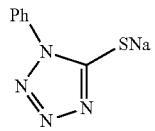

(10a)

1-phenyl-1H-tetrazole-5-thiol (30.0 g) was dissolved in methanol (200 ml) and sodium methoxide (10.0 g) was added thereto at 0° C. The reaction liquid was stirred at room temperature for 1 hour and concentrated leaving the solvent (50 ml), and diisopropyl ether (400 ml) was added thereto, followed by stirring for 1 hour. The precipitated solid was filtered and washed with diisopropyl ether (400 ml) to give the title compound (30.1 g).

$^1$H-NMR (400 MHz, DMSO-d$_6$) δ 8.03-7.99 (m, 2H), 7.49-7.44 (m, 2H), 7.37-7.32 (m, 1H)

Example 8

Preparation of Sodium 1-tert-butyl tetrazole-5-thiolate (10b)

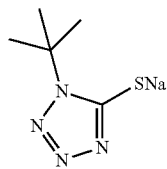

(10b)

The procedure was carried out in the same manner as in Example 7, except that 1-tert-butyl-1H-tetrazole-5-thiol (15.8 g) was used in place of 1-phenyl-1H-tetrazole-5-thiol. The title compound was obtained (16.1 g).

$^1$H-NMR (400 MHz, DMSO-d$_6$) δ 1.42 (s, 9H)

Example 9

Preparation of Sodium 1-methyl-1H-benzo[d]imidazole-2-thiolate (10c)

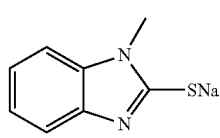

(10c)

The procedure was carried out in the same manner as in Example 7, except that 1-methyl-1H-benzo[d]imidazole-2-thiol (16.4 g) was used in place of 1-phenyl-1H-tetrazole-5-thiol (30.0 g). The title compound was obtained (17.4 g).

$^1$H-NMR (400 MHz, DMSO-d$_6$) δ 7.69-7.60 (m, 2H), 7.49-7.44 (m, 2H), 3.8 (s, 3H)

Example 10

Preparation of Sodium benzo[d]thiazole-2-thiolate (10d)

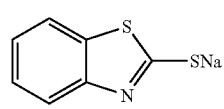

(10d)

The procedure was carried out in the same manner as in Example 7, except that benzo[d]thiazole-2-thiol (16.3 g) was used in place of 1-phenyl-1H-tetrazole-5-thiol (30.0 g). The title compound was obtained (16.6 g).

$^1$H-NMR (400 MHz, DMSO-d$_6$) δ 8.31-8.21 (m, 1H), 8.11-8.02 (m, 1H), 7.52-7.44 (m, 2H)

Example 11

Preparation of 2-methyl-1-phenylpropan-2-yl 2-((4R,6S)-2,2-dimethyl-6-((1-phenyl-1H-tetrazol-5-ylthio)methyl)-1,3-dioxan-4-yl)acetate (11a)

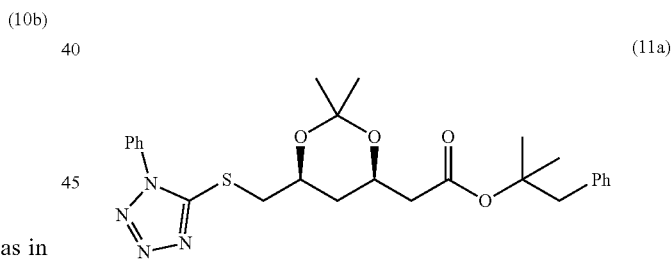

(11a)

2-methyl-1-phenylpropan-2-yl 2-((4R,6S)-6-(chloromethyl)-2,2-dimethyl-1,3-dioxan-4-yl)acetate (30 g) prepared in Example 5 was dissolved in dimethylformamide (150 ml), and sodium 1-phenyl-1H-tetrazole-5-thiolate (33.9 g) prepared in Example 7 was added thereto. The reaction liquid was warmed to 90° C. and then stirred for 24 hours. The reaction liquid was cooled to room temperature, and diisopropyl ether (600 ml) and purified water (600 ml) were added thereto. The organic layer was separated, washed with purified water (600 ml), a 10% sodium bicarbonate aqueous solution (600 ml), a saturated ammonium chloride aqueous solution (600 ml) and a saturated sodium chloride aqueous solution (600 ml), dried over anhydrous magnesium sulfate, filtered, and then concentrated under reduced pressure to give the title compound (40.8 g).

$^1$H-NMR (400 MHz, CDCl$_3$) δ 7.60-7.52 (m, 5H), 7.28-7.16 (m, 5H), 4.26-4.21 (m, 2H), 3.66-3.59 (m, 1H), 3.39-

3.34 (m, 1H), 3.10-2.96 (dd, 2H), 2.47-2.41 (m, 1H), 2.34-2.28 (m, 1H), 1.71-1.67 (m, 1H), 1.46-1.24 (m, 13H)

Example 12

Preparation of 2-methyl-1-phenylpropan-2-yl 2-((4R, 6S)-6-((1-tert-butyl-1H-tetrazol-5-ylthio)methyl)-2,2-dimethyl-1,3-dioxan-4-yl)acetate (11b)

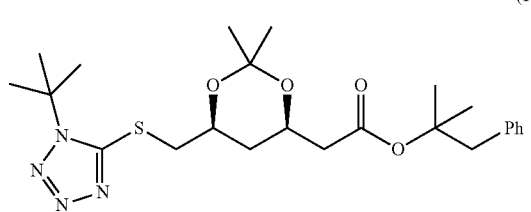

(11b)

The procedure was carried out in the same manner as in Example 11, except that sodium 1-tert-butyl tetrazole-5-thiolate (3.6 g) prepared in Example 8 was used in place of sodium 1-phenyl-1H-tetrazole-5-thiolate, and 3.5 g of 2-methyl-1-phenylpropan-2-yl 2-((4R,6S)-6-(chloromethyl)-2,2-dimethyl-1,3-dioxan-4-yl)acetate was used in place of 30 g thereof. The title compound was obtained (4.6 g).

$^1$H-NMR (400 MHz, CDCl$_3$) δ 7.52-7.22 (m, 5H), 4.26-4.21 (m, 2H), 3.69-3.59 (m, 1H), 3.32-3.31 (m, 1H), 3.08-2.95 (dd, 2H), 2.47-2.41 (m, 1H), 2.34-2.28 (m, 1H), 1.71-1.67 (m, 1H), 1.46-1.24 (m, 22H)

Example 13

Preparation of 2-methyl-1-phenylpropan-2-yl 2-((4R, 6S)-2,2-dimethyl-6-((1-methyl-1H-benzo[d]imidazol-2-ylthio)methyl)-1,3-dioxan-4-yl)acetate (11c)

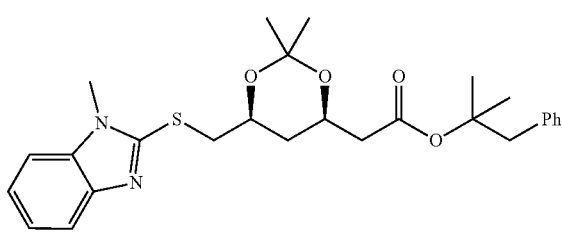

(11c)

The procedure was carried out in the same manner as in Example 11, except that 3.5 g of 2-methyl-1-phenylpropan-2-yl 2-((4R,6S)-6-(chloromethyl)-2,2-dimethyl-1,3-dioxan-4-yl)acetate was used in place of 30 g thereof, and sodium 1-methyl-1H-benzo[d]imidazole-2-thiolate (3.7 g) prepared in Example 9 was used in place of sodium 1-phenyl-1H-tetrazole-5-thiolate. The title compound was obtained (4.7 g).

$^1$H-NMR (400 MHz, CDCl$_3$) δ 7.60-7.21 (m, 9H), 4.32-4.28 (m, 2H), 3.72 (s, 3H), 3.62-3.59 (m, 1H), 3.39-3.32 (m, 1H), 3.10-2.95 (dd, 2H), 2.47-2.41 (m, 1H), 2.34-2.28 (m, 1H), 1.71-1.67 (m, 1H), 1.46-1.24 (m, 13H)

Example 14

Preparation of 2-methyl-1-phenylpropan-2-yl 2-((4R, 6S)-6-((benzo[d]thiazol-2-ylthio)methyl)-2,2-dimethyl-1,3-dioxan-4-yl)acetate (11d)

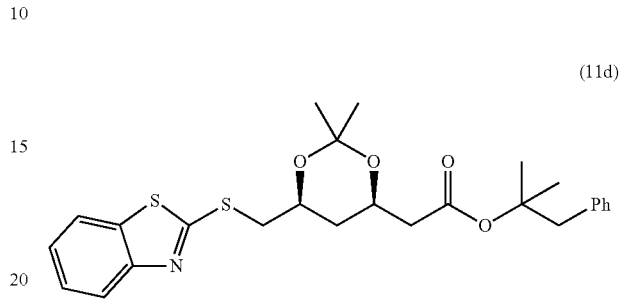

(11d)

The procedure was carried out in the same manner as in Example 11, except that 3.5 g of 2-methyl-1-phenylpropan-2-yl 2-((4R,6S)-6-(chloromethyl)-2,2-dimethyl-1,3-dioxan-4-yl)acetate was used in place of 30 g thereof, and sodium benzo[d]thiazole-2-thiolate (3.8 g) prepared in Example 10 was used in place of sodium 1-phenyl-1H-tetrazole-5-thiolate. The title compound was obtained (4.6 g).

$^1$H-NMR (400 MHz, CDCl$_3$) δ 8.18-8.05 (m, 1H), 8.05-7.92 (m, 1H), 7.60-7.21 (m, 7H), 4.33-4.29 (m, 2H), 3.61-3.59 (m, 1H), 3.41-3.38 (m, 1H), 3.15-2.94 (dd, 2H), 2.51-2.49 (m, 1H), 2.31-2.28 (m, 1H), 1.69-1.65 (m, 1H), 1.45-1.23 (m, 13H)

Example 15

Preparation of 2-methyl-1-phenylpropan-2-yl 2-((4R, 6S)-2,2-dimethyl-6-((1-phenyl-1H-tetrazol-5-ylsulfonyl)methyl)-1,3-dioxan-4-yl)acetate (1a)

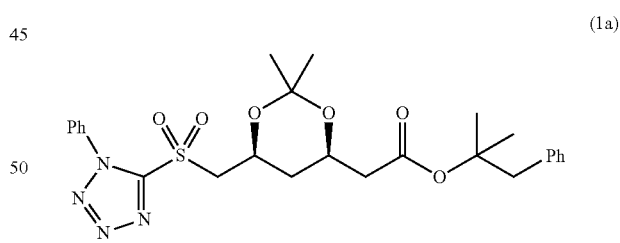

(1a)

2-methyl-1-phenylpropan-2-yl 2-((4R,6S)-2,2-dimethyl-6-((1-phenyl-1H-tetrazol-5-ylthio)methyl)-1,3-dioxan-4-yl)acetate (19.6 g) prepared in Example 11 was dissolved in diisopropyl alcohol (200 ml), and a mixed solution of 30% hydrogen peroxide (44.8 ml) and ammonium heptamolybdate tetrahydrate (4.8 g) was added thereto at 0° C. The reaction liquid was warmed to room temperature and stirred for 30 hours. Then, ethyl acetate (400 ml) and purified water (400 ml) were added to the reaction liquid, followed by separation the organic layer, and 10% sodium thiosulfate (200 ml) was added to the organic layer, followed by stirring for 30 minutes. The organic layer was separated, washed with a saturated sodium chloride aqueous solution (300 ml), dried over anhydrous magnesium sulfate, filtered, and then concentrated under reduced pressure to give the title compound (20.3 g).

$^1$H-NMR (400 MHz, CDCl$_3$) δ 7.66-7.58 (m, 5H), 7.30-7.21 (m, 3H), 7.19-7.14 (m, 2H), 4.50-4.44 (m, 1H), 4.22-4.08 (m, 1H), 3.46-3.32 (m, 2H), 3.08-2.95 (m, 2H), 2.43-2.37 (m, 1H), 2.29-2.23 (m, 1H), 1.68-1.38 (m, 8H), 1.30-1.15 (m, 6H)

Example 16

Preparation of 2-methyl-1-phenylpropan-2-yl 2-((4R,6S)-6-((1-tert-butyl-1H-tetrazol-5-ylsulfonyl)methyl)-2,2-dimethyl-1,3-dioxan-4-yl)acetate (1b)

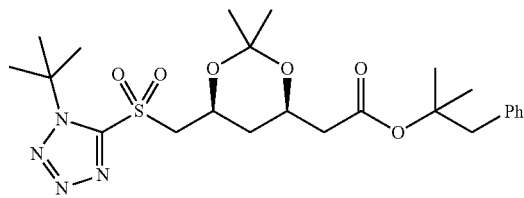

(1b)

The procedure was carried out in the same manner as in Example 15, except that 2-methyl-1-phenylpropan-2-yl 2-((4R,6S)-6-((1-tert-butyl-1H-tetrazol-5-ylthio)methyl)-2,2-dimethyl-1,3-dioxan-4-yl)acetate (3.5 g) prepared in Example 12 was used in place of 2-methyl-1-phenylpropan-2-yl 2-((4R,6S)-2,2-dimethyl-6-((1-phenyl-1H-tetrazol-5-ylthio)methyl)-1,3-dioxan-4-yl)acetate (19.6 g). The title compound was obtained (3.6 g).

$^1$H-NMR (400 MHz, CDCl$_3$) δ 7.52-7.22 (m, 5H), 4.30-4.25 (m, 2H), 3.72-3.61 (m, 1H), 3.42-3.31 (m, 1H), 3.15-2.98 (dd, 2H), 2.52-2.45 (m, 1H), 2.35-2.30 (m, 1H), 1.69-1.65 (m, 1H), 1.45-1.21 (m, 22H)

Example 17

Preparation of 2-methyl-1-phenylpropan-2-yl 2-((4R,6S)-2,2-dimethyl-6-((1-methyl-1H-benzo[d]imidazol-2-ylsulfonyl)methyl)-1,3-dioxan-4-yl)acetate (1c)

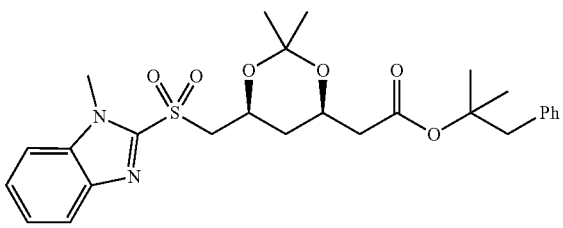

(1c)

The procedure was carried out in the same manner as in Example 15, except that 2-methyl-1-phenylpropan-2-yl 2-((4R,6S)-2,2-dimethyl-6-((1-methyl-1H-benzo[d]imidazol-2-ylthio)methyl)-1,3-dioxan-4-yl)acetate (4.8 g) prepared in Example 13 was used in place of 2-methyl-1-phenylpropan-2-yl 2-((4R,6S)-2,2-dimethyl-6-((1-phenyl-1H-tetrazol-5-ylthio)methyl)-1,3-dioxan-4-yl)acetate (19.6 g). The title compound was obtained (5.1 g).

$^1$H-NMR (400 MHz, CDCl$_3$) δ 7.70-7.19 (m, 9H), 4.42-4.38 (m, 2H), 3.72 (s, 3H), 3.69-3.59 (m, 1H), 3.42-3.39 (m, 1H), 3.20-2.98 (dd, 2H), 2.57-2.51 (m, 1H), 2.24-2.28 (m, 1H), 1.73-1.67 (m, 1H), 1.47-1.21 (m, 13H)

Example 18

Preparation of 2-methyl-1-phenylpropan-2-yl 2-((4R,6S)-6-((benzo[d]thiazol-2-ylsulfonyl)methyl)-2,2-dimethyl-1,3-dioxan-4-yl)acetate (1d)

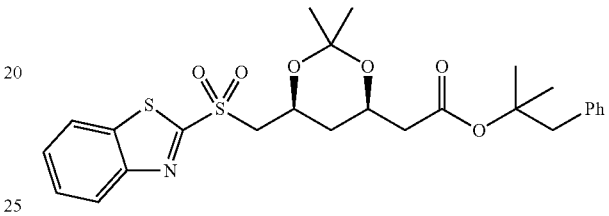

(1d)

The procedure was carried out in the same manner as in Example 15, except that 2-methyl-1-phenylpropan-2-yl 2-((4R,6S)-6-((benzo[d]thiazol-2-ylthio)methyl)-2,2-dimethyl-1,3-dioxan-4-yl)acetate (4.8 g) prepared in Example 14 was used in place of 2-methyl-1-phenylpropan-2-yl 2-((4R,6S)-2,2-dimethyl-6-((1-phenyl-1H-tetrazol-5-ylthio)methyl)-1,3-dioxan-4-yl)acetate (19.6 g). The title compound was obtained (5.0 g).

$^1$H-NMR (400 MHz, CDCl$_3$) δ 8.41-8.31 (m, 1H), 8.12-8.02 (m, 1H), 7.60-7.21 (m, 7H), 4.33-4.29 (m, 2H), 3.61-3.59 (m, 1H), 3.41-3.38 (m, 1H), 3.14-2.96 (dd, 2H), 2.55-2.51 (m, 1H), 2.31-2.28 (m, 1H), 1.71-1.66 (m, 1H), 1.48-1.21 (m, 13H)

Example 19

Preparation of 2-methyl-1-phenylpropan-2-yl 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate (3)

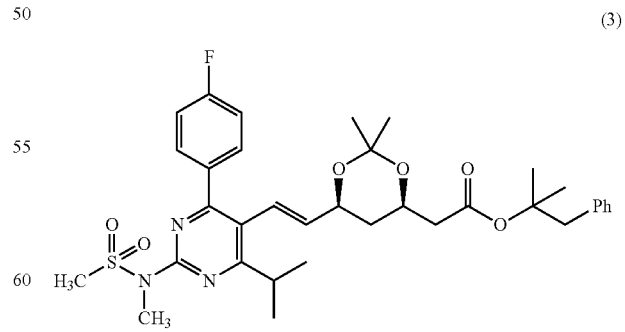

(3)

2-methyl-1-phenylpropan-2-yl-2-((4R,6S)-2,2-dimethyl-6-((1-phenyl-1H-tetrazol-5-ylsulfonyl)methyl)-1,3-dioxan-4-yl)acetate (25.75 g) prepared in Example 15 and N-(4-(4-fluorophenyl)-5-formyl-6-isopropylpyrimidin-2-yl)-N- methylmethanesulfonamide (15.55 g) were dissolved in tetrahydrofuran (60 ml), followed by cooling to −78° C. under an argon atmosphere, and lithium bis(trimethylsilyl)amide (120 ml of a 0.5M solution in tetrahydrofuran) was added thereto over 10 minutes, followed by stirring at the same temperature for 2 hours. Then, the mixture was stirred for 4 hours while warming to 0° C. A saturated ammonium chloride aqueous solution (250 ml) was added to the reaction liquid, followed by stirring for 10 minutes, and ethyl acetate (500 ml) was added thereto. The organic layer was separated and washed successively with purified water (250 ml), a saturated sodium bicarbonate aqueous solution (250 ml,) and a saturated sodium chloride aqueous solution (250 ml), dried over anhydrous magnesium sulfate, filtered, and then concentrated under reduced pressure. The resulting solid was stirred with isopropyl ether, filtered and collected. This solid was dried in a vacuum oven overnight (50° C., 200 mbar) to give the title compound (26.06 g, 90%).

$^1$H-NMR (400 MHz, CDCl$_3$) δ 7.66-7.63 (m, 2H), 7.29-7.05 (m, 7H), 6.52-6.48 (dd, 1H), 5.48-5.43 (dd, 1H), 4.43-4.37 (m, 1H), 4.32-4.21 (m, 1H), 3.60 (s, 3H), 3.53 (s, 3H), 3.39-3.36 (m, 1H), 3.12-2.99 (dd, 2H), 2.50-2.27 (m, 2H), 1.51-1.37 (m, 14H), 1.28-1.10 (m, 7H)

Example 20

Preparation of (E)-7-[4-(4-fluorophenyl)-6-isopropyl-2-[methyl(methylsulfonyl)amino]pyrimidin-5-yl](3R,5S)-3,5-dihydroxyhept-6-enoic Acid Hemicalcium Salt (Rosuvastatin Hemicalcium Salt)

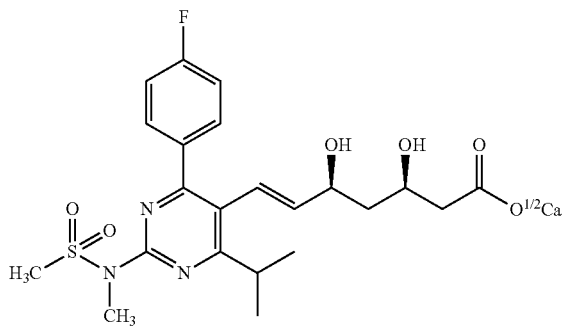

2-methyl-1-phenylpropan-2-yl 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate (15.38 g) prepared in Example 19 was dissolved in tetrahydrofuran (80 ml) and a 0.1M hydrochloric acid aqueous solution (19.21 ml) was added thereto, followed by stirring for 24 hours while heating to 40° C. The reaction liquid was cooled to room temperature and a 0.5M sodium hydroxide aqueous solution (81 ml) was added thereto over 5 minutes, followed by stirring for 4 hours. Ethyl acetate (250 ml) and purified water (250 ml) were added to the reaction liquid, and the organic layer was separated, washed with saturated sodium chloride (150 ml), dried over anhydrous sodium sulfate, filtered, and then concentrated under reduced pressure to give (E)-7-[4-(4-fluorophenyl)-6-isopropyl-2-[methyl(methylsulfonyl)amino]pyrimidin-5-yl](3R,5S)-3,5-dihydroxyhept-6-enoic acid sodium salt.

The obtained (E)-7-[4-(4-fluorophenyl)-6-isopropyl-2-[methyl(methylsulfonyl)amino]pyrimidin-5-yl](3R,5S)-3,5-dihydroxyhept-6-enoic acid sodium salt was dissolved in acetonitrile (100 ml), and purified water (190 ml) and a 1.0M hydrochloric acid aqueous solution (81 ml) were added thereto at 0° C., followed by stirring for 1 hour. Diisopropyl ether (250 ml) was added to the reaction liquid, followed by separation of the organic layer, and acetonitrile (81 ml) and a 40% methyl amine aqueous solution (7.3 ml) were added thereto at 0° C., followed by stirring at room temperature for 3 hours. The reaction liquid was stirred at 0° C. for 1 hour, and the precipitated solid was filtered, washed with acetonitrile (100 ml) and then dried under reduced pressure at 50° C. for 4 hours to give a (E)-7-[4-(4-fluorophenyl)-6-isopropyl-2-[methyl(methylsulfonyl)amino]pyrimidin-5-yl](3R,5S)-3,5-dihydroxyhept-6-enoic acid methylamine salt (10.25 g). Purified water (60 ml) was added to the solid to which a 2M sodium hydroxide aqueous solution (10 ml) was then added, followed by stirring for 1 hour, and the reaction solvent was distilled off under reduced pressure. Purified water (100 ml) was additionally added thereto, followed by another distillation under reduced pressure. To the resulting oil was added purified water (60 ml), and anhydrous calcium chloride (3.0 g) dissolved in purified water (10 ml) was added thereto, followed by stirring for 1 hour. The precipitated solid was filtered and washed with purified water (100 ml) to give the title compound (8.5 g, 77%). [α]$_D^{20}$ was +7.2 in 1% methanol, and the chiral purity was 99.9% ee, as confirmed by a HPLC method using the following chiral column.

Chiral HPLC Method
Column: Chiracel OJ-R [Cellulose tris(4-methylbenzoate)] (4.6 mm×50 mm, 5 μm)
Mobile phase: Mixture of acetonitrile and 0.1% trifluoroacetic acid (250:750)
Detector: UV spectrophotometer (measuring wavelength: 242 nm)
Flow rate: 0.5 mL/min
Column temperature: 35° C.
Injection volume: 10 μl
Analysis time: 75 min $^1$H-NMR (400 MHz, DMSO-d$_6$) δ 7.72-7.68 (m, 2H), 7.27 (t, 2H), 6.49 (d, 1H), 5.52 (dd, 1H), 4.20-4.18 (m, 1H), 3.74 (m, 1H), 3.53 (s, 3H), 3.43-3.41 (m, 4H), 2.14-2.09 (m, 1H), 2.00-1.96 (m, 1H), 1.51-1.48 (m, 1H), 1.32-1.28 (m, 1H), 1.21-1.17 (m, 6H).

Comparative Example 1

Preparation of Rosuvastatin Hemicalcium Salt from N-(5-((diphenylphosphoryl)methyl)-4-(4-fluorophenyl)-6-isopropylpyrimidin-2-yl)-N-methylmethanesulfonamide (DPPO) Described in WO 00/49014

N-(5-((diphenylphosphoryl)methyl)-4-(4-fluorophenyl)-6-isopropylpyrimidin-2-yl)-N-methylmethanesulfonamide (20 g) was dissolved in tetrahydrofuran (240 ml) at 40° C., and then inactivated by repeated applications of vacuum and argon five times. This solution was cooled to −78° C. under an argon atmosphere, and sodium bis(trimethylsilyl)amide (39 ml of a 1.0M solution in tetrahydrofuran) was added thereto over 10 minutes. The dropping funnel was rinsed with tetrahydrofuran (10 ml), followed by stirring for 1 hour, and t-butyl 2-((4R,6S)-6-formyl-2,2-dimethyl-1,3-dioxan-4-yl)acetate (84.5 ml of a ca. 13.5% w/w toluene solution) was added portionwise thereto over 20 minutes. The dropping funnel was rinsed with toluene (20 ml), and the mixture was stirred for another 15 minutes at −78° C. and then stirred while warming to 10° C. over about 1.5 hours. To the reaction liquid was added a 20% acetic acid aqueous solution (15 ml), followed by stirring for 10 minutes.

The mixture was concentrated by distillation under atmospheric pressure (jacket 110° C.) at 93° C. to thereby collect the total distillate (270 ml). The concentrated mixture was cooled to 40° C., and water (40 ml) was added thereto. Then, the mixture was further stirred for 5 minutes and allowed to precipitate for 15 minutes. The lower aqueous phase was discarded, a 7% (w/w) sodium bicarbonate aqueous solution (40 ml) was added, and the mixture was stirred for 5 minutes, followed by precipitation for 15 minutes. The lower aqueous phase was discarded, water (30 ml) was added, and the mixture was further stirred for 5 minutes and allowed to precipitate for 15 minutes. The aqueous phase was discarded.

The organic phase was charged to distillation equipment containing toluene (20 ml), and distilled under atmospheric pressure (jacket 125 to 130° C.) at 116° C. to collect 86 ml of a distillate. Following a vacuum treatment, 17 ml of a distillate was additionally collected at a temperature of 111° C. Vacuum was released, and the concentrated mixture was cooled to 80° C. Warmed MeOH (140 ml, 50° C.) was added thereto under high-speed stirring, followed by cooling to 20° C. for 30 minutes. The resulting suspension was further cooled to 2° C. for 30 minutes, and the solid was collected by filtration, washed with cold MeOH (60 ml, 2° C.), collected in a dried state, and dried in a vacuum oven overnight (50° C., 200 mbar) to obtain BEM (14.61 g) as a desired compound. A mixture of BEM (5.0 g) and acetonitrile (35 ml) was stirred at 40° C. under an inert atmosphere. To the resulting solution was added 0.02M hydrochloric acid (9.5 ml) over 30 minutes, and the temperature was maintained at 35 to 42° C. The mixture was stirred at 40° C. for 3 hours and then cooled to 25° C. A 1.0M sodium hydroxide solution (9.5 ml) was added with stirring thereto at 25° C. and the mixture was stirred for another 1 hour at 25° C. Sodium chloride (4.7 g) was added and the mixture was cooled to −5° C. over 1 hour. A solution of 1M hydrochloric acid (9.5 ml) and sodium chloride (2.4 g) was added thereto at −5° C. to achieve a pH of 3.4 to 4.0, and the mixture was stirred at the same temperature for 5 minutes. The mixture was allowed to precipitate at −5° C. for 10 minutes to obtain two layers. The lower layer was separated and discarded. Acetonitrile (65 ml) at −5° C. was added to the remaining solution, and the mixture was filtered through a filter. A 40% methylamine solution (1.1 ml) in water was added at −5° C., and the mixture was warmed to 30° C. over 40 minutes. This temperature was maintained for 90 minutes. Thereafter, the mixture was cooled to 0° C. for 40 minutes, and this temperature was maintained for 90 minutes. The resulting solid was collected by filtration, and washed with acetonitrile (2×12 ml). This solid was dried at 35° C. under vacuum (3.5 g). 2M aqueous sodium hydroxide (5.44 ml) was added to a stirred mixture of a methylamine salt (6.0 g) in deaerated water (30 ml) at 20° C., and the mixture was stirred for 1 hour. The mixture was filtered, and concentrated under reduced pressure at 40° C. until 24 ml of a distillate was collected. Water (24 ml) was added thereto, and the mixture was concentrated again under reduced pressure at 40° C. until 24 ml of a distillate was collected. Water (30 ml) was added thereto, and a solution of calcium chloride dihydrate (1.03 g) in water (6 ml) was added dropwise at 20° C. The mixture was stirred for 45 minutes, and the resulting solid was filtered. The solid was washed with water (36 ml) and dried under vacuum at 40° C. to give a (E)-7-[4-(4-fluorophenyl)-6-isopropyl-2-[methyl(methylsulfonyl)amino]pyrimidin-5-yl](3R,5S)-3,5-dihydroxyhept-6-enoic acid hemicalcium salt (5.27 g, 48%).

Experimental Example

Production Yield of Rosuvastatin Hemicalcium Salts

The total production yield of a rosuvastatin hemicalcium salt was compared between the process of Reaction Scheme 3 representing the method for preparing a rosuvastatin hemicalcium salt in accordance with the present invention, as described in the Detailed Description of the present invention, and the process of Reaction Scheme 1 (WO 00/49014, see Comparative Example 1) and Reaction Scheme 2 (WO 07/125547) representing a known method for preparing a rosuvastatin hemicalcium salt. The results are given in Table 1 below.

TABLE 1

| | Examples | Comparative Example 1 (WO 00/49014) | WO 07/125547 |
|---|---|---|---|
| Yield | 69% | 48% | 41% |

That is, novel intermediate compounds of a rosuvastatin hemicalcium salt in accordance with the present invention and a preparation method using the same exhibited 21% and 28% increases in yield of a rosuvastatin hemicalcium salt, as compared to WO 00/49014 (section denoted by Reaction Scheme 1 in the present specification) and WO 07/125547 (section denoted by Reaction Scheme 2 in the present specification) which are the corresponding known preparation methods.

What is claimed is:
1. A method for preparing a compound of formula 3, comprising:
reacting a compound of formula 1:

[Formula 1]

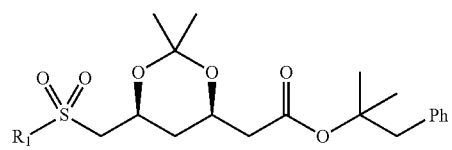

wherein:
$R_1$ represents

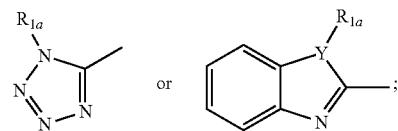

Y represents a nitrogen or sulfur atom; and
$R_{1a}$ represents hydrogen, $C_1$-$C_4$ alkyl or phenyl
with a compound of formula 2:

[Formula 2]

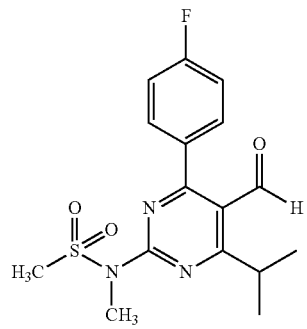

in the presence of a base to prepare the compound of formula 3:

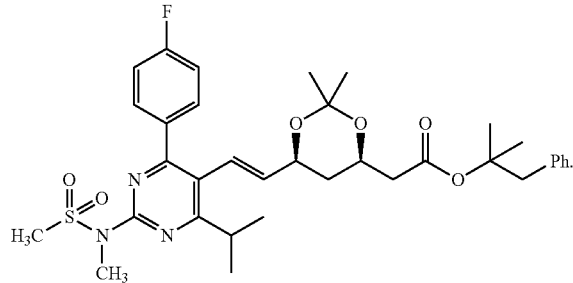 [SMILES: CC(C)c1nc(N(C)S(C)(=O)=O)nc(-c2ccc(F)cc2)c1/C=C/[C@@H]1C[C@H](CC(=O)OC(C)(C)Cc2ccccc2)OC(C)(C)O1]

2. The method of claim 1, wherein the reaction is carried out at a temperature of −90 to 0° C.

3. The method of claim 1, wherein the base is selected from among lithium bis(trimethylsilyl)amide, sodium bis(trimethylsilyl)amide and potassium bis(trimethylsilyl)amide.

4. A compound of Formula 1:

[Formula 1]

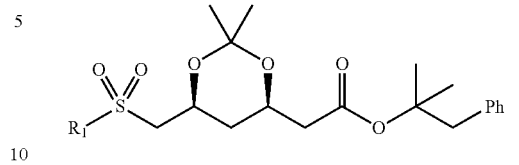

wherein:

$R_1$ represents

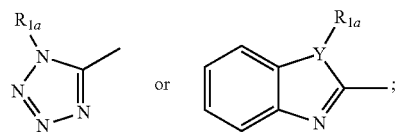

Y represents a nitrogen or sulfur atom; and $R_{1a}$ represents hydrogen, $C_1$-$C_4$ alkyl or phenyl.

5. The method of claim 2, wherein the base is selected from among lithium bis(trimethylsilyl)amide, sodium bis(trimethylsilyl)amide and potassium bis(trimethylsilyl)amide.

* * * * *

UNITED STATES PATENT AND TRADEMARK OFFICE
CERTIFICATE OF CORRECTION

PATENT NO. : 8,524,914 B2
APPLICATION NO. : 13/376173
DATED : September 3, 2013
INVENTOR(S) : Lee et al.

Page 1 of 1

It is certified that error appears in the above-identified patent and that said Letters Patent is hereby corrected as shown below:

IN THE TITLE PAGES:

In Item (75) Inventors:
Page 1, line 5, "Hongwoo Lee, Hwaseong-si (KR)" should read —Hongwoo Lee, Gyeonggi-do (KR)—.

In Item (75) Inventors:
Page 1, line 6, "Daejong Park, Gunpo-si (KR)" should read —Daejong Park, Gyeonggi-do (KR)—.

In Item (75) Inventors:
Page 1, lines 8-9, "Hohyung Ryu, Cheonan-si (KR)" should read —Hohyung Ryu, Chungcheongnam-do (KR)—.

In Item (75) Inventors:
Page 1, lines 9-10, "Dongjin Kim, Cheonan-si (KR)" should read —Dongjin Kim, Chungcheongnam-do (KR)—.

Signed and Sealed this
Eighteenth Day of March, 2014

Michelle K. Lee
*Deputy Director of the United States Patent and Trademark Office*